United States Patent
Hjelme et al.

(10) Patent No.: US 7,440,110 B2
(45) Date of Patent: Oct. 21, 2008

(54) OPTICAL SENSING OF MEASURANDS

(75) Inventors: Dag R. Hjelme, Trondheim (NO); Arne Berg, Kattem (NO); Reinold Ellingsen, Trondheim (NO); Berit Falch, Trondheim (NO); Astrid Bjørkøy, Spogndal (NO); Dan Østling, Trondheim (NO)

(73) Assignee: Invivosense ASA, Trondheim (NO)

( * ) Notice: Subject to any disclaimer, the term of this patent is extended or adjusted under 35 U.S.C. 154(b) by 908 days.

(21) Appl. No.: 10/273,483

(22) Filed: Oct. 18, 2002

(65) Prior Publication Data

US 2003/0112443 A1    Jun. 19, 2003

Related U.S. Application Data

(60) Provisional application No. 60/346,941, filed on Oct. 19, 2001.

(51) Int. Cl.
*G01B 9/02*    (2006.01)

(52) U.S. Cl. .................................................. 356/477

(58) Field of Classification Search ............... 356/450, 356/477–493, 497, 495
See application file for complete search history.

(56) References Cited

U.S. PATENT DOCUMENTS

| | | | | |
|---|---|---|---|---|
| 4,743,113 A | * | 5/1988 | Jubinski ................. | 356/478 |
| 4,778,987 A | * | 10/1988 | Saaski et al. .............. | 250/226 |
| 5,015,843 A | | 5/1991 | Seitz et al. ............. | 250/227.21 |
| 5,623,561 A | | 4/1997 | Hartman .................... | 385/12 |
| 5,744,794 A | * | 4/1998 | Michie et al. ........... | 250/227.16 |
| 5,917,966 A | | 6/1999 | Beuhler et al. ................. | 385/12 |
| 6,051,437 A | * | 4/2000 | Luo et al. .................... | 436/172 |
| 6,097,487 A | * | 8/2000 | Kringlebotn et al. ........ | 356/450 |
| 6,335,793 B1 | * | 1/2002 | Freeman et al. ............. | 356/477 |
| 6,590,665 B2 | * | 7/2003 | Painchaud et al. ........... | 356/480 |
| 6,671,055 B1 | * | 12/2003 | Wavering et al. ............ | 356/478 |
| 7,003,184 B2 | * | 2/2006 | Ronnekleiv et al. ........... | 385/12 |

FOREIGN PATENT DOCUMENTS

| | | |
|---|---|---|
| EP | 0 450 782 A2 | 3/1991 |
| GB | 2 198 844 A | 6/1988 |
| GB | 2 228 082 A | 8/1990 |
| GB | 2 340 231 A | 2/2000 |

OTHER PUBLICATIONS

N. Fabricius et al. "A Gas Sensor Based on an Integrated Optical Mach-Zehnder Interferometer", Sensors and Actuators B., Elsevier Sequoia S.A. Lausanne, Switzerland, vol. B07, No. 1/3; Mar. 1, 1992, pp. 672-676.

Y. Liu et at, "An Integrated Optical Sensor for Measuring Glucose Concentration"; Applied Physics B. Photo-physics and Laser Chemistry, Springer Verlag. Heidelberg, Germany; vol. B54, No. 1, 1992, pp. 18-23.

PCT Search Report Serial No. PCT/GB02/04760 dated Feb. 27, 2003.

* cited by examiner

*Primary Examiner*—Hwa S Lee (Andrew)
(74) *Attorney, Agent, or Firm*—McCormick, Paulding & Huber LLP

(57) ABSTRACT

A chemical sensing probe comprises an optical fiber or may be mounted on an optical fiber. The probe has a chemically sensitive measuring material which exhibits a change in volume and/or a change in refractive index in the presence of a given chemical. The change in volume and/or refractive index gives a change in an optical path length through the probe which can be measured interferometrically.

52 Claims, 11 Drawing Sheets

- Y: Antibody-immobilized
- ↷●↶: Antigen-immobilized
- ●: Free-antigen

OPTICAL SENSING OF MEASURANDS

This application claims the benefit of U.S. Provisional Application No. 60/346,941, filed Oct. 19, 2001, which is hereby incorporated by reference in its entirety.

BACKGROUND OF THE INVENTION

1. Technical Field

This invention relates to the fiber-optic sensing of chemical and non-chemical measurands particularly, although not exclusively, within the body. The invention relates to in-vivo medical applications and also to ex-vivo or in-vitro medical uses or non-medical uses.

2. Background of the Invention

With the advance of technology relating to medical diagnosis and therapy, there is an on-going need to improve methods and systems for sensing chemical parameters, particularly in a medical context both outside and within the body. There is also a need more generally to improve the sensitivity and cost effectiveness with which various chemical species can be detected.

There are many optical techniques known in the art for sensing various chemical parameters. For example, U.S. Pat. No. 5,132,057 discloses an optical fiber probe based on the immobilisation of fluorescent dye in a hydrogel at the distal end of the optical fiber. The dye is excited by passing light to it from the optical fiber and the intensity of the fluorescence is monitored to give an indication of blood pH.

It is also known from U.S. Pat. No. 5,804,453 to immobilise a reagent such as an antigen layer at the end of an optical fiber. When placed in a solution containing the complementary antibodies, an antibody layer binds to the antigen layer. This growth in the immobilised layers is detected by a change in the phase difference between light reflected from the fiber/reagent boundary and the distal edge of the immobilised layers respectively.

Furthermore U.S. Pat. No. 5,898,004 discloses a device composed of a crystalline colloidal array polymerized in a hydrogel. Swelling of the hydrogel in response to stimuli is measured as a shift in the Bragg diffraction wavelength.

DISCLOSURE OF THE INVENTION

There remains a need, however, for a highly sensitive probe capable of sensing a wide range of chemicals. Accordingly, when viewed from a first aspect the present invention provides an interferometric chemical sensing probe comprising or for mounting to an optical fiber, and a chemically responsive measuring material adapted to exhibit a change in volume and/or refractive index in the presence of a given chemical so as to produce a change in at least one optical path length through the probe.

Thus it will be seen by those skilled in the art that in accordance with the present invention there is provided a sensor probe which is operable to sense a chemical by its effect on a measuring material which produces a change in optical path length which may be measured interferometrically.

When viewed from a second aspect therefore the invention provides a method of sensing a chemical comprising providing a probe including a measuring material that changes in volume and/or refractive index in the presence of said chemical, exposing said measuring material to said chemical and measuring interferometrically the resulting change in an optical path length through the probe.

Optical path length is dependent both on the physical length of the path traversed by light and on the refractive index of that path. Thus, in accordance with the invention in its broadest terms either of these parameters or both of them may be affected by the measuring material.

Any suitable measuring material may be used but preferably the measuring material comprises a cross-linked polymer. The cross-linked polymer may change in volume as a result of the target analyte binding to it. This may be because cross-links in the polymer network are broken or because the analyte changes the affinity of the polymer chains to the solvent containing the analyte. The refractive index of the polymer be changed simply as a result of the volume change (i.e. if the polymer swells it will become more rarefied and so its refractive index will fall) and/or because analyte molecules bind to the polymer chains.

It will be appreciated that the use of a cross-linked polymer in an interferometric sensor probe is novel and inventive in its own right—for measuring any parameter not just chemical sensing. Thus when viewed from a further aspect the invention provides an interferometric sensing probe comprising or for mounting to an optical fiber, and a cross-linked polymer adapted to exhibit a change in volume and/or refractive index in response to a given measurand so as to produce a change in at least one optical path length through the probe.

Except where otherwise specified, hereinafter references to a measuring material are to be taken to be include a reference to the cross-linked polymer of the foregoing aspect of the invention.

Preferably the probe is arranged such that the optical path in question is between the two reflectors of a Fabry-Perot interferometer. As is well known to those skilled in the art, a Fabry-Perot interferometer provides a sharp fringe pattern. Shifts in the resulting interference pattern can then be used as a sensitive measure of changes in the optical path length within the measuring material.

In some preferred embodiments the distal reflector of the measuring cavity is formed by the boundary between the measuring material and the external environment of the probe—i.e. the peripheral edge of the measuring material. In a particularly simple preferred embodiment for example, the measuring material is provided at the end of the optical fiber and its respective boundaries with the fiber and its environment provide the two reflectors of the interferometer.

Alternatively, as in some preferred embodiments, a separate reflector is provided. By using a separate reflector rather than relying on the reflection occurring at the boundary between the polymer and its environment, the strength of the reflected light signal may be significantly enhanced. As will be appreciated, a reflector may reflect substantially all incident light whereas the reflection coefficient at a boundary between two media of similar refractive indices will be relatively low.

Where provided, the reflector may be fixed, i.e. the measuring cavity comprises an etalon. This will be used when a pure refractive index change in the measuring material is being measured. In other preferred embodiments however, the reflector is arranged so as to be moved by the measuring material as it changes in volume.

Such an arrangement is novel and inventive in its own right and thus when viewed from a further aspect the invention may be seen to provide an optical sensing probe comprising a measuring material adapted to undergo a change in volume in response to a given measurand; and a reflector coupled to the measuring material so as to be moved by it as it changes in volume, thereby changing the length of a light path through the apparatus.

The measuring material preferably comprises a cross-linked polymer, most preferably sensitive to a predetermined chemical.

If a separate reflector is provided it is not essential that light passes through the measuring material. Instead the light may traverse a path whose length is affected by the change in volume of the measuring material (by virtue of including the movable reflector) without passing through it. This could be beneficial in a number of circumstances. For example it allows non-transparent measuring materials to be used. It also obviates the disadvantages of scattering or photo degradation which might be caused by passing light through the measuring material.

In one set of examples of such an arrangement, the measuring light is incident upon the reflector on the same side which is coupled to the measuring side, but in a different region thereof. In a particularly preferred embodiment, the measuring material is arranged in the form of a hollow cylinder and the light is arranged to pass through the middle of the cylinder to the reflector at one end. This is beneficial in allowing the measuring material to come into contact with the medium containing the measurand around the entire periphery of the cylinder.

In another preferred embodiment, the measuring material is arranged to act upon the reflector on the face opposite that which reflects the measuring light.

In fact, even without a separate reflector the measuring light need not pass through the measuring material in order for its optical path to be influenced by a change in volume of the measuring material. Thus in a broad set of preferred embodiments the probe is arranged such that variable optical path through the probe does not include the measuring material.

As mentioned hereinbefore, in its broadest terms, the invention is applicable to measuring materials which exhibit a change in volume, a change in refractive index or both in response to the chemical or other measurand. The Applicants have appreciated that it is desirable in some circumstances to restrict the change in the optical path length to a change in the refractive index only. This could, for example, be because only the refractive index changes—i.e. there is no increase or reduction in the volume of the polymer. Alternatively, one may choose to measure only the refractive index component of the response to a given measurand.

Accordingly, in some preferred embodiments, the apparatus is arranged such that the physical length of the optical path traversed by the measuring beam does not change in response to the analyte being measured. In other words, the measuring material is provided in a fixed-length etalon through which the light passes in use.

If the physical path length is fixed, the measuring light will be required to pass through the measuring material. If the measuring material is one which is suitable for passing light through it, it will be appreciated that, a much greater effect will be yielded than if the measuring material influences only the evanescent field of the incident beam. Also, in accordance with the invention a refractive index change may take place throughout the volume of the material rather than just a surface layer thereof, e.g. where a cross-linked polymer is used. This makes better use of the optical energy.

In a preferred embodiment of this arrangement, a portion of measuring material is provided in a cavity of fixed-length (in the direction parallel to the propagation of the measuring light), but is free to expand in a direction orthogonal to the path of the measuring light. This allows the use of measuring materials which incidentally expand as well as undergoing a change in refractive index. It is even conceivable with such an arrangement that both the refractive index change and the volume change may be measured independently of one another by two separate measuring beams. By making the cavity open to lateral expansion, contact between the measuring material and the analyte is facilitated.

In an alternative embodiment, the measuring material may be incorporated as part of the core of a wave guide. For example, part of the core of a D-profile optical fiber may be removed and replaced with the polymer. This would allow the change in effective refractive index of the fiber to be measured and also allows interaction between the analyte and the measuring material. This arrangement should be contrasted with known D-fibers which have a coating on the flat side whose refractive index change can only directly influence the evanescent field of the light beam passing through the fiber.

Any suitable interferometric measurement technique may be employed to measure the change in optical path length produced in accordance with the invention. Preferably the reflection spectrum is measured using a scanning filter. This allows the free spectral range and phase of the interferogram to be extracted thereby allowing the optical path length to be deduced. Most preferably the apparatus described in U.S. Pat. No. 6,097,487 is used. Using the built-in reference grating and comb filter allows the absolute wavelength axis to be accessed which ensures accuracy and long-term stability.

Potential alternative read-out systems include white light interferometry, which gives an absolute measurement of free spectral range but with limited resolution; and dual or multi-wavelength modulated laser interrogation, which should give very accurate phase measurement. A technique based on Fourier transform spectroscopy could also be used.

Probes in accordance with the invention may be used as described to sense chemical analytes. In some circumstances however it may be advantageous to compensate for environmental parameters such as temperature, pressure pH, salt concentration, dissolved proteins etc., in the measurements obtained. Preferably therefore, compensation means is provided for compensating for environmental parameters. Any suitable known means of measurement could be used to provide a compensating measurement. For example a fiber Bragg grating (FBG) could be written into the optical fiber.

Alternatively, the compensation means comprises a Fabry-Perot interferometer—i.e. similar to that used to measure the target analyte in preferred embodiments. In some preferred embodiments the compensation means comprises a cross-linked polymer with a different response to the target analyte—e.g. it may have a lower density of recognition components bound to the polymer chains.

Alternatively a different material may be used—e.g. one of known response to the environmental parameters. In an exemplary such embodiment, the probe comprises an intermediate substrate layer between the measuring material and the end of the optical fiber. This provides temperature compensation if the substrate has a similar thermal expansion coefficient to the measuring material or at least a known relationship to it.

Preferably, the substrate layer is provided with means, such as a suitable indent, to locate the optical fiber. This provides more reliable lateral positioning of the optical fiber with respect to the measuring material.

In a yet further alternative, the compensation means may comprise the same measuring material as is used to sense the target analyte but simply not be exposed to the analyte is use. This is particularly advantageous where, as is preferred, the measuring material comprises a hydrogel as these have been found to have a very large coefficient of thermal expansion and are thus able to provide sensitive temperature compensation.

In exemplary embodiments, two portions of the measuring material are provided at the distal end of an optical fiber, separated by a layer which acts to reflect a proportion of the light incident on it. This is required since there would otherwise be no boundary to reflect the light. If only temperature and/or pressure compensation is required, the partially reflective layer may be impermeable. However if compensation for pH or dissolved substances is required, a membrane is required to pass solution to the compensation portion of measuring material, but to block the analyte. The partially reflective layer may provide this membrane. Alternatively, the membrane may be provided separately—e.g. on the side wall of a cylinder of the device. If provided, the partially reflective layer need have no membrane function in this arrangement.

Where the compensation means comprises a Fabry-Perot interferometer, it may be provided in parallel with the probe for measuring the target analyte. For example in one preferred embodiment measurement and compensation cavities are provided adjacent one another on a common support. This is advantageous since it ensures as far as possible that the compensation cavity reacts to the environmental parameters in the same way as the measurement cavity—e.g. because they may be manufactured together and they will experience the same degree of thermal expansion, pressure etc.

In such an arrangement the two cavities are preferably interrogated by separate optical fibers. Separate optical analysers may be provided but preferably an optical switch is provided to enable a common analyser to measure both cavities. The switching and measurement times are typically negligible in comparison to the response time of the cavities to the analyte or changes in the environmental parameters.

The use of optical fibers in such embodiments is beneficial since the overall probe may be relatively small, making it suitable for human in-vivo use. For example two optical fibers adjacent one another will typically have a width of the order of only a quarter of a millimetre. Furthermore, small quantities of the measuring and compensation materials may be used giving fast response times and small minimum sample volumes.

In other preferred embodiments the compensation means is provided in series with the measurement part of the probe. Some such embodiments are described above—for example where a FBG is written into the optical fiber or where two portions of the same measuring material are provided at the end of a fiber. A further set of embodiments have a measuring material and a compensation material provided coaxially at the distal end of an optical fiber, optionally separated by a partially reflective layer. Preferably the two materials are covered by a membrane sleeve or a capillary tube. As before, it may not be necessary to expose the compensation material to the analyte solution—e.g. if only temperature or pressure compensation is required.

The possibility has been described above of using an intermediate substrate to provide compensation in the measurements e.g. for temperature fluctuations. More generally an intermediate substrate layer can be beneficial, particularly in probes suitable for ex-vivo use, since it allows the measuring material to be separate from the optical fiber. This leads to a reduction in the manufacturing cost. It also allows the measuring material to be provided on a test strip separate from a measuring device. Thus some embodiments preferably comprise an intermediate substrate layer between the optical fiber and the measuring material.

Where such a substrate is provided it may be directly optically coupled to the fiber, but preferably an intermediate lens is provided—most preferably a graded index (GRIN) lens. This is advantageous since it allows a thicker substrate to be used as compared to an arrangement with no such lens since the measuring beam is not constrained by the numerical aperture of the fibre.

In fact in some circumstances if a lens or lens system is provided in the path of the measuring beam upstream of the optical cavity influenced by the measuring material, it is not necessary to provide an optical fiber coupling the probe to the associated read-out instrumentation. Thus, when viewed from a further aspect, the present invention provides an apparatus for sensing a chemical interferometrically comprising a substrate bearing a chemically responsive measuring material adapted to exhibit a change in volume and/or refractive index in the presence of a given chemical so as to produce a change in at least one optical path length through the apparatus, and at least one lens through which in use light traversing said optical path passes.

This arrangement is advantageous in that it allows the measuring material to be provided on a, preferably disposable, test strip, separate from the lens and other read-out instrumentation.

The measuring material is preferably arranged in accordance with one or more of the preferred features set out hereinabove with reference to arrangements including an optical fiber.

The invention also extends to the other aspects of the invention set out hereinabove with the optical fiber replaced with a lens and substrate.

The cross-linked polymer used in accordance with any of the foregoing aspects of the invention will depend upon the analyte being measured. Preferably a water-swollen cross-linked polymeric network—i.e. a hydrogel is used. Preferably the hydrogel comprises a gel monomer e.g. acrylamide and a cross-linking agent e.g. bisacrylamide. As well as polyacrylamide, other suitable hydrogels include polyvinyl alcohol and polyhydroxyethyl methacrylate.

In one embodiment, additional cross-links are formed between antibodies and antigens immobilised on the polymer chains. This antigen could either be a native antigen (i.e. natural protein) or a peptide sequence similar to a linear epitope on the native antigen. Such a hydrogel will swell in the presence of a free antigen because antigen-antibody cross-linked binding can be disassociated by exchange of the immobilised antigen for the free antigen. In the absence of the free antigen, the gel will shrink.

In another embodiment, the gel comprises a biomolecular recognition component linked to the polymer chain. Such linking may be direct or indirect through one or more linking molecules. Examples of such biomolecular recognition components include enzymes, antibodies, antigens and aptamers. The hydrogel volume changes when a chemical species binds to the recognition component and changes the hydrophobicity of the gel. Alternatively, the hydrogel refractive index will change when analyte molecules bind to the recognition component.

In most cases there will be a combination of both volume change and refractive index change. In a case with cross-links formed between antibodies and antigens, the concentration of antibodies might be so low that the dissociation by exchange of immobilized antigen for free antigen results in an insignificant refractive index change whereas the volume change will be large and therefore dominate. On the other hand in a case where only the recognition component, e.g. antibody, is immobilized (in sufficiently high concentration), the binding of antigen with no net charge to the antibody will result in insignificant swelling, however the refractive index change will be large and therefore dominate. With charged antigens the volume change can be significant such that both effects contribute.

In some preferred embodiments of the invention, a porous membrane is provided through which analytes and solvent may diffuse. The pore size is chosen such that the membrane molecular weight cut-off is well above the molecular weight of the analyte being measured. Such a membrane might also be used to block large molecules, and/or blood cells from reaching the measuring material by choosing a sufficiently small pore size. Examples of suitable membrane materials are nitrocellulose, cellulose acetate, polycarbonate, Teflon, nylon, and polyestersulfone. Preferably, the membrane material is cast onto a mechanical support member to ensure sufficient mechanical strength.

Examples of receptor ligand pairs include anti-BSA IgG and BSA (Bovine Serum Albumin), anti-CRP IgG and CRP (C-Reactive Protein), and anti-Troponin IgG and Troponin.

The measuring material, e.g. hydrogel or other cross-linked polymer may be formed directly onto the optical fiber. In some preferred such embodiments, a gel is formed by immobilising the polymer material on the end of the fiber, covering with a lid of sufficient optical quality, and performing the gelation. The lid may thereafter be removed e.g in solution. This method is novel and inventive in its own right and thus when viewed from a further aspect the present invention provides a method of forming a gel on the end of an optical fiber comprising immobilising a pre-gel material on said fiber end, covering said pre-gel material with a lid, performing a gelation of the pre-gel material to form a gel and removing said lid.

Preferably the pre-gel material is laterally constrained by a suitable containment means. Preferred examples of such a containment means are a capillary tube or a cylinder cast. The cylinder cast preferably comprises part of a fiber optic connector.

Alternatively, in some preferred embodiments, a separate probe element comprising the measuring material is formed and subsequently mounted to an optical fiber. This facilitates manufacture as it is then no longer to manipulate the whole fiber during fabrication.

Although so far only passive measurements of the optical path length through a probe in accordance with the invention have been discussed, this is not the only option. The various probes described hereinabove may also be used as active sensors—i.e. the sensor cavity could be used as part of a laser cavity. In such arrangements the sensor cavity would be coupled to the main laser cavity—i.e. that formed by the fiber itself, preferably with gain. This may also be seen as the sensor cavity providing external optical feedback to the laser.

In accordance with all of the foregoing embodiments, the optical fiber could either be a multimode fiber (large core) or single mode (small core) of standard dimensions. The measuring material is preferably between 10 and 1000 microns, most preferably between 100 and 200 micrometres Where a capillary tube is provided it preferably has an inner diameter of approximately 130 micrometres (assuming a fiber of nominal size 125 micrometres) and an outer diameter of approximately 600 micrometres. Where a ferrule is provided on the optical fiber, it is preferably of inner diameter 128 micrometres and outer diameter 2.5 millimetres.

DESCRIPTION OF THE DRAWINGS

Certain preferred embodiments of the present invention will now be described by way of example only, with reference to the accompanying drawings in which.

DETAILED DESCRIPTION OF THE INVENTION

Figure 1:
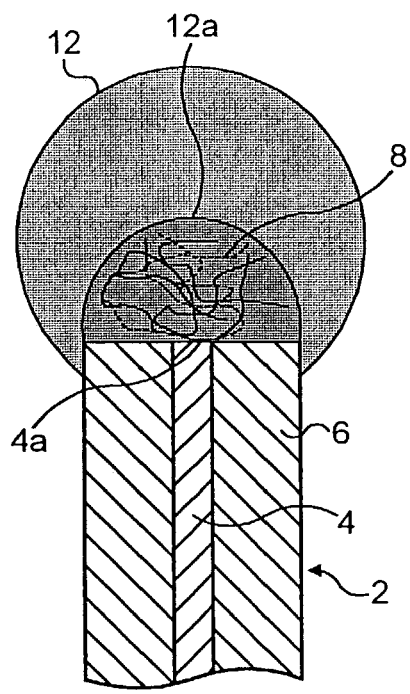
FIG. 1 is a cross sectional view of sensor probe embodying the present invention.

Turning to FIG. 1, a first embodiment of the invention is shown. An optical fiber 2 comprising a core 4 and a cladding 6 has a cross-linked polymer hydrogel 8 formed at one end. The gel 8 is immobilised on the tip of the fiber 2 using a silanization technique, well known per se in the art. To ensure uniform gelation with an optical quality surface, the gelation is performed in an oxygen-free humid atmosphere provided by delivering nitrogen passed through a water column to the curing chamber.

Figure 2:
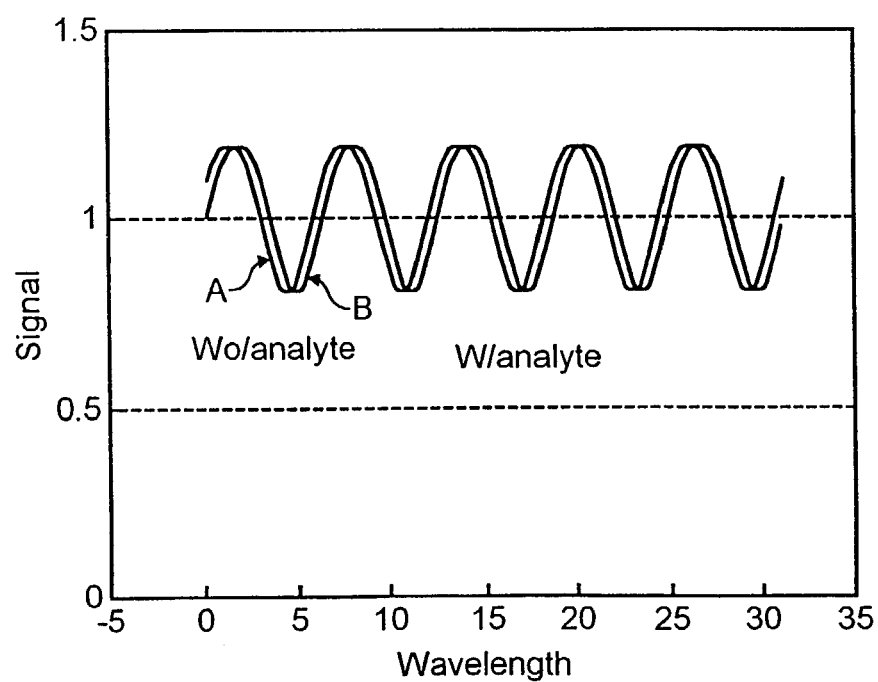
FIG. 2 is a graph of wavelength versus amplitude showing the reflection spectrum of the probe of FIG. 1.

In use, a beam of light is passed along the optical fiber core 4. A portion of the light is reflected back from the boundary 4a between the fiber core 4 and the hydrogel 8. This forms the reference beam for a Fabry-Perot interferometer. The rest of the light is transmitted into the hydrogel 8 which forms a cavity between the fiber core/hydrogel boundary 4a and the hydrogel/external boundary 12a. The light beam reflected back from this cavity causes an interference pattern which may be seen as curve A on the graph of FIG. 2.

Figure 3:
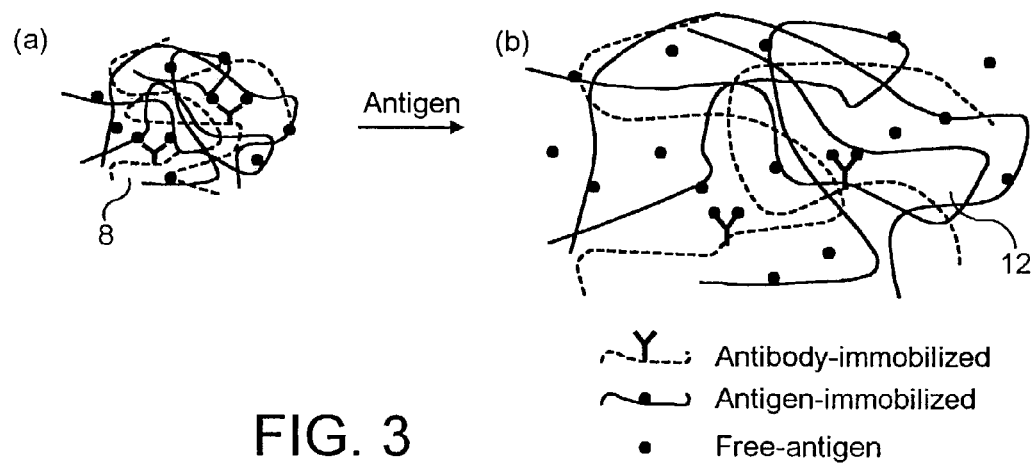
FIG. 3a is a schematic depiction of a cross-linked polymer.
FIG. 3b is a schematic depiction of a cross-linked polymer with some cross-links disassociated.

The free end of the sensor is then placed into a solution containing the target analyte 12. This could, for example, be in-vivo, in which case the probe will be suitably sterilized. When the hydrogel 8 comes into contact with the analyte 12, the hydrogel 8 will change in volume and/or refractive index. In one example, the hydrogel comprises an acrylamide gel monomer and a bisacrylamide cross-linking agent. Additional cross-links are formed between antibodies and antigens immobilised on the polymer chains (FIG. 3*a*). In the presence of a free antigen in the solution 12, the hydrogel 8 will swell since the additional cross-link binding is disassociated by exchange of the immobilised antigen for the free antigen (FIG. 3*b*).

As the hydrogel 8 swells, the physical length of the path of the light through it is increased. Correspondingly, the wavelengths at which constructive and destructive interference with the reference beam occur are shifted slightly. This is shown by curve B in FIG. 2.

By measuring this shift in wavelength, the swelling of the hydrogel may be calculated and hence the concentration of analyte may be deduced. The wavelength shift is measured using a scanning filter as described in U.S. Pat. No. 6,097,487.

Figure 4:
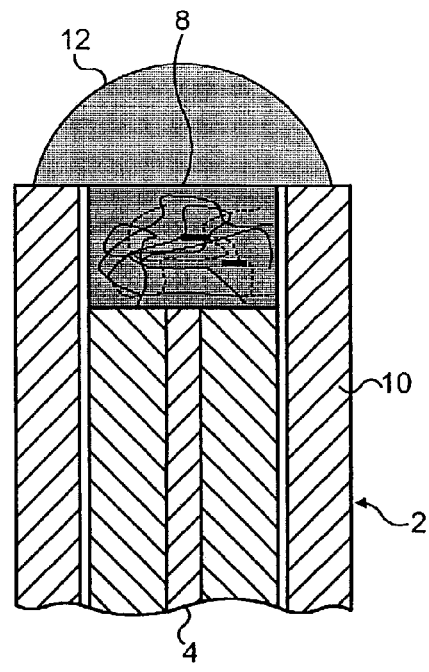
FIG. 4 shows a second embodiment, similar to that of FIG. 1 but with the addition of a capillary tube.

FIG. 4 shows an embodiment identical to FIG. 1 except for the addition of a capillary tube 10 which acts as a sleeve around the optical fiber 2 and hydrogel 8. The capillary tube 10 makes the overall probe more robust and prevents it from bending. The capillary tube 10 also allows the hydrogel 8 to be formed by a slightly different method. In this method gelation is performed by closing the end of the capillary tube 10 with an optical quality glass slide (not shown). The glass slide is removed in solution after complete gelation, exposing an optical quality gel surface.

Figure 18:
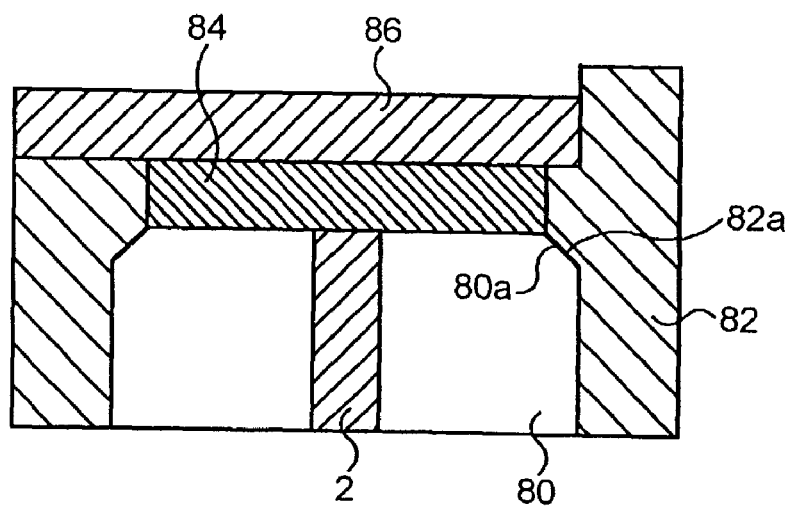
FIG. 18 shows a method of forming a hydrogel layer on the end of an optical fiber.

A similar method of casting a hydrogel 8 onto the end of an optical fiber 2 is may be seen with reference to FIG. 18. In this arrangement, the fiber 2 is encased in a ferrule 80 to form one half a standard fiber optic connector. A metal cylinder cast 82 is fitted around the ferrule 80. The cylinder 82 has a tapered neck 82*a* to engage a tapered mating surface 80*a* of the fiber ferrule. The tapered surfaces 80*a*, 82*a* ensure that the fiber 2 is not inserted fully into the cylinder 82 and thus a space is formed between the end of the ferrule 80 and inner side wall of the cylinder cast 82. Pre-gel material 84 is placed in this space. An optical quality glass slide 86 is then placed over the pre-gel material 84 in order to perform gelation. Again, of the lid is removed in solution after gelation to leave an optical quality gel surface.

Figure 5:
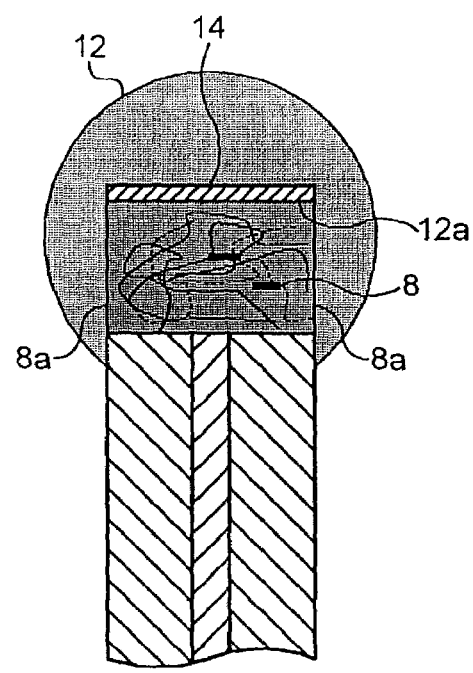
FIG. 5 shows a third embodiment, similar to the first embodiment but including a reflector moved by the polymer gel.

FIG. 5 shows an alternative embodiment in which a reflector 14 is provided at the distal edge 12*a* of the hydrogel 8. The reflector 14 ensures higher reflection at of the hydrogel boundary 12*a*, thereby amplifying the interference spectrum to be measured. Contact between of the hydrogel 8 and of the analyte 12 now takes place on of the outer side face 8*a* of the hydrogel. As in of the embodiment of FIGS. 1 and 4, of the optical path length through this probe is affected by changes in both of the volume and of the refractive index of the hydrogel 8.

Figure 6:
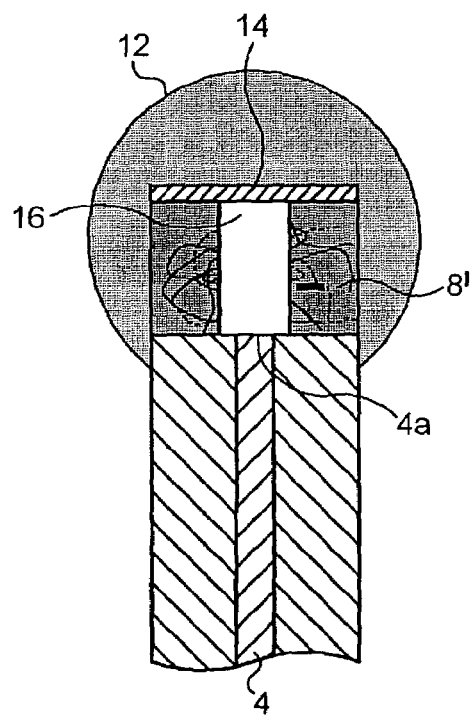
FIG. 6 shows a fourth embodiment including a reflector.

FIG. 6 shows an embodiment similar to FIG. 5, but in which of the hydrogel 8' is formed as a hollow cylinder. Of the hollow centre 16 of the cylinder is aligned with of the end of the optical fiber core 4. This means that light transmitted through of the boundary 4*a* at of the end of the fiber core 4, passes through of the centre 16 of the cylinder before being reflected by of the reflector 14, rather than passing through of the hydrogel 8'.

Of the result is that this sensor arrangement is not sensitive to any changes in of the refractive index of the hydrogel 8' brought about by its contact with of the dissolved analyte 12, but rather will measure only a change in volume of the hydrogel 8'. Such a change in volume causes vertical movement of the reflector 14 attached to it and thus modifies the physical length of the cavity formed between the end 4*a* of the fiber core and the reflector 14.

This arrangement is useful, for example, where there is no change in the refractive index of the hydrogel or where it is desired to separate the volume change from the refractive index change.

In a potential modified embodiment (not shown) an expandable/contactable cylinder may be provided around the inner surface of the hydrogel cylinder 8' in order to prevent the ingress of the analyte solution 12.

Figure 7:
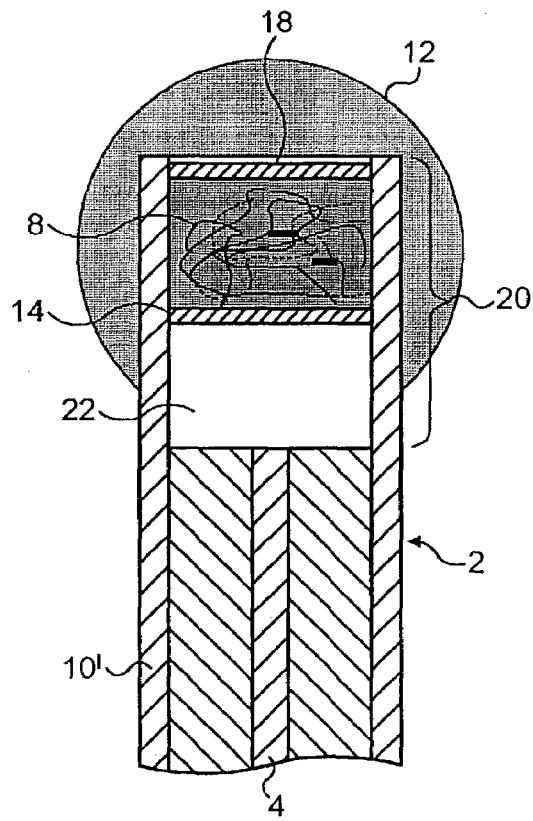
FIG. 7 shows a fifth embodiment including a reflector and a membrane.

A further embodiment is shown in FIG. 7. In common with the embodiment of FIG. 4, in this embodiment the optical fiber 2 is encased in a capillary tube 10'. However, in this embodiment the capillary tube 10' extends further beyond the end of the optical fiber 2 and is closed at its distal end by a porous membrane 18. The membrane 18 has a pore size sufficiently large to allow the ingress of the target analyte, but sufficiently small to prevent larger particles e.g. blood cells from passing through. Examples of suitable membrane materials include nitrocellulose, cellulose acetate, polycarbonate, Teflon, nylon and polyestersulfone. The membrane 18, together with the optical fiber 2, defines a space 20 inside the capillary tube 10'. The space 20 is approximately half-filled at its upper end with hydrogel 8. A reflector 14 is attached to the lower face of the gel with its reflective surface facing towards the optical fiber 2. An optical cavity is thus defined between the reflector 14 and the optical fiber 2.

In use, the membrane 18 allows analyte to come into contact with the hydrogel 8 thereby causing it to swell. This will move the reflector downwards and therefore shorten the optical path of light traversing the cavity 22. This is in contrast to the previous embodiment in which swelling of the hydrogel causes an increase in the path length. In common with the previous embodiment however, the light does not pass through the hydrogel 8 and is not therefore affected by any changes in its refractive index. Instead, only volume changes of the hydrogel 8 will affect the optical path length travelled by the measuring beam of light.

In an alternative embodiment (not shown) the reflector 14 of FIG. 7 may be omitted and the edge of the hydrogel 8 is used to reflect the incident light.

Figure 8:
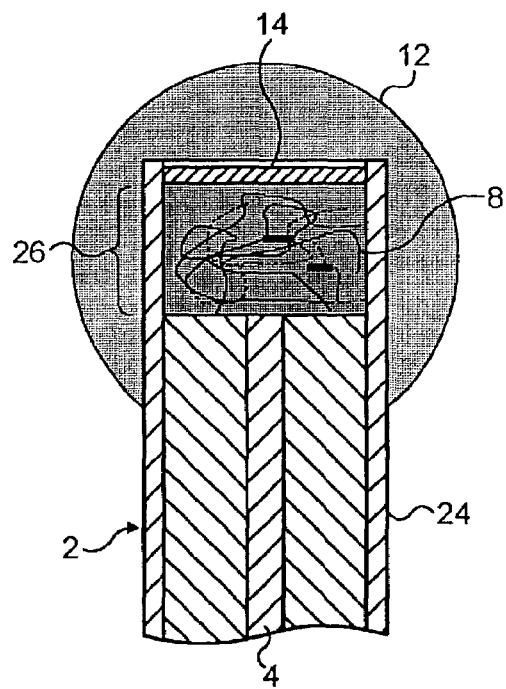
FIG. 8 shows a further embodiment in which the reflector is fixed.

A yet further embodiment is shown in FIG. 8. In this embodiment, the optical fiber 2 is encased in a porous membrane sleeve 24. The membrane sleeve 24 extends beyond the end of the optical fiber 2 and is closed at the far end by a reflector 14, thus defining a cavity 26 at the end of the optical fiber 2 which is completely filled with hydrogel 8. In this embodiment, the cavity 26 has a fixed volume and the hydrogel 8 cannot therefore expand in response to the target analyte.

Instead, the hydrogel 8 changes in refractive index in the presence of the target analyte. This alters the optical path length and hence shifts the interference pattern just as a change in the physical path length does. The hydrogel in this embodiment comprises a gel monomer, a cross-linking agent and a biomolecular recognition component linked to the polymer chain, directly or through one or more linking molecules. Examples of such biomolecular components include enzymes, antibodies, antigens, and aptamers. The refractive index change is brought about when analyte molecules bind to the recognition component linked to the polymer chain.

Figure 9A:
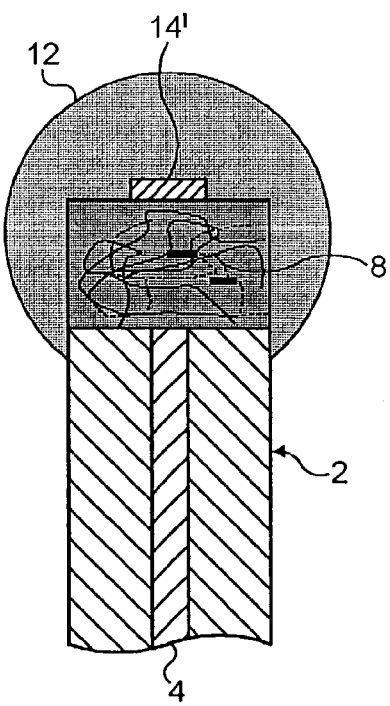
FIGS. 9a and 9b are respectively embodiments with and without a capillary tube utilising a relatively small reflector.

As may be seen from the embodiment of FIG. 9*a*, if a separate reflector 14' is provided, it need not extend the full width of the optical fiber 2 and hydrogel 8. The reason for this is that light emerges from the optical fiber core 4 through a relatively small range of angles. The reduced area reflector 14' is therefore sufficient to reflect light transmitted from the fiber core 4 and through the hydrogel 8 back into the core. It also means that it takes less time for the anlayte to diffuse throughout the measuring material.

Figure 9B:
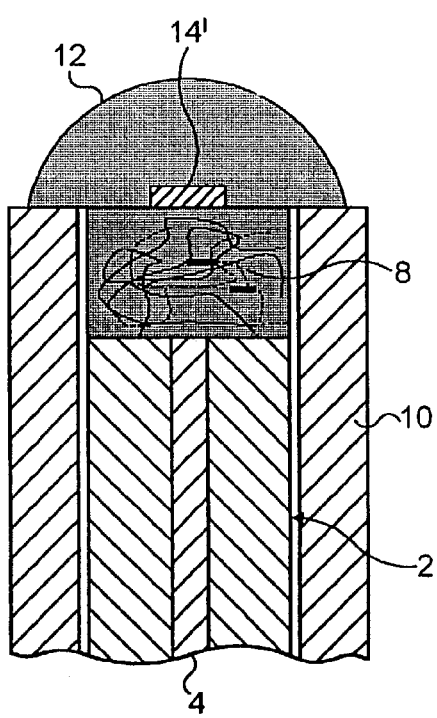

FIG. 9b shows a variant of the embodiment of FIG. 9a where the hydrogel 8 is immobilised in an open cavity formed at the end of a capillary tube 10 in which the optical fiber 2 is received. It will be appreciated that in this embodiment, the reduced size of the reflector 14' is particularly advantageous because it allows the hydrogel 8 to come into contact with the analyte solution 12 without requiring a porous membrane.

Figure 10:
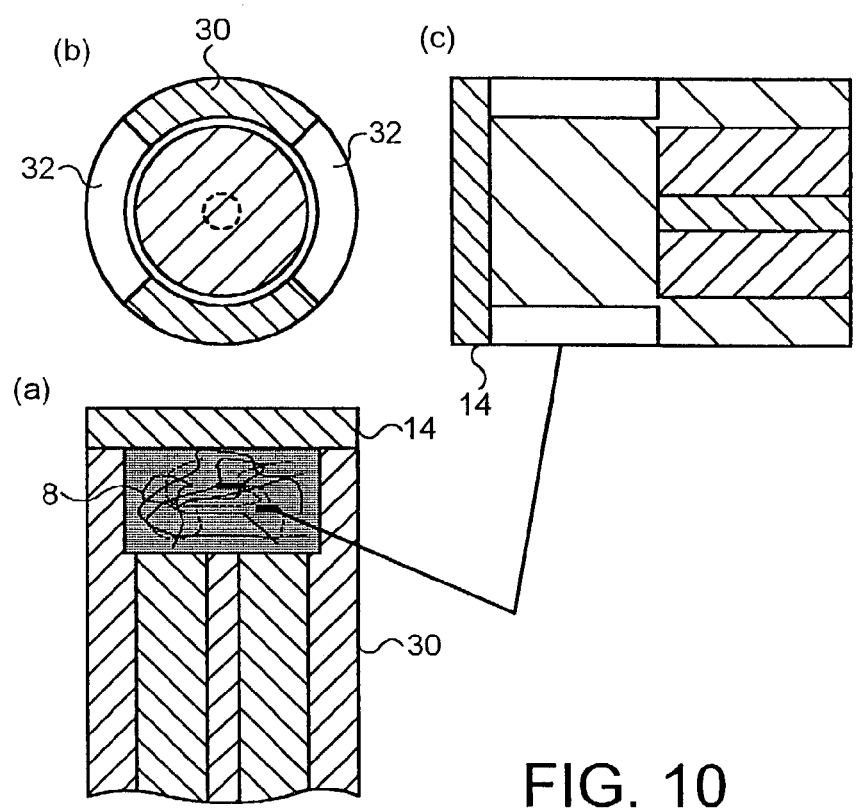
FIG. 10 shows a yet further embodiment of the invention which does not require a membrane.

FIGS. 10a to 10c show a variant on the embodiment in FIG. 8. in which instead of a porous sleeve 24, a capillary tube 30 may be used, thereby giving better rigidity. However, to allow contact between the hydrogel 8 and the analyte 12, the capillary tube 30 has two diametrically opposed cut-outs 32 at the upper end thereof. These form, together with the reflector 14, side windows which allow contact between the hydrogel 8 and the analyte. They also allow expansion of the hydrogel 8 in a lateral direction, although this will not have any effect on the vertical optical path traversed by the measuring beam of light.

Figure 11:
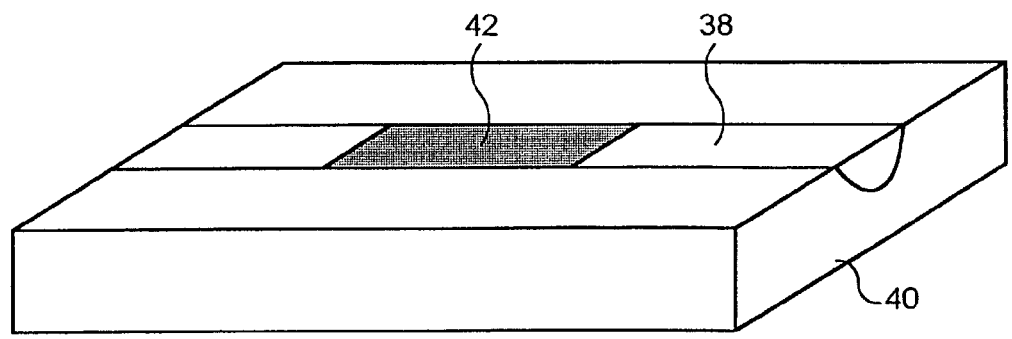
FIG. 11 shows a further embodiment of the invention in which the polymer gel is provided in an optical waveguide.

A yet further embodiment of the invention is shown in FIG. 11. In this embodiment, an optical waveguide 38 is defined in a substrate layer 40. A longitudinal section 42 of the waveguide 38, is, however, replaced by a cross-linked polymer gel 42. The two boundaries between the gel 42 and the waveguide 38 form the two reflectors of a Fabry-Perot cavity. This may be interrogated by a beam of light as previously described and may thus sense changes in the refractive index of the polymer gel 42 in response to a target analyte. The cavity 42 is fixed in length and so volume changes are not relevant.

In an alternative embodiment (not shown) the gel has a smaller transverse dimension than the waveguide mode and thus lateral expansion may affect the effective refractive index of the waveguide.

Figure 12A:
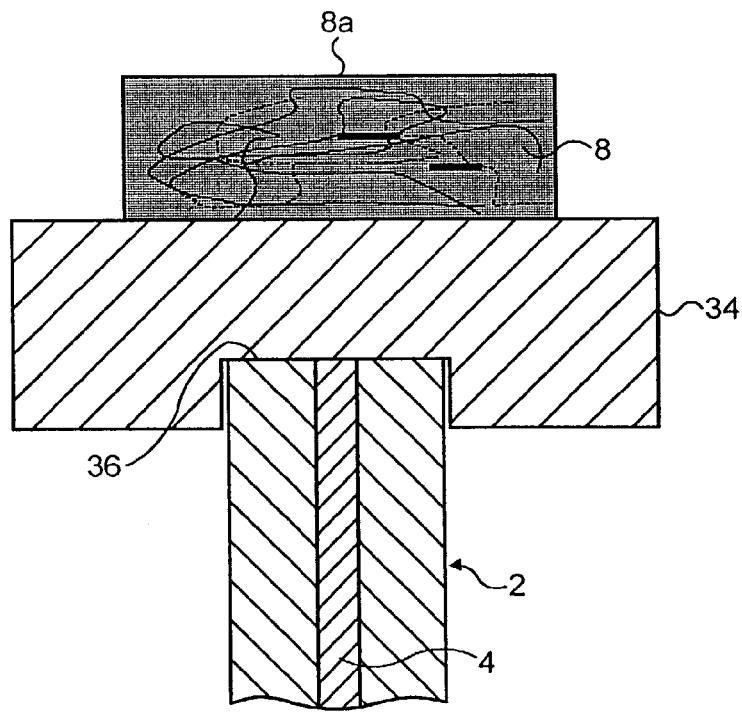
FIGS. 12a, 12b show respectively further embodiments utilising a substrate layer with and without a reflector.

FIG. 12a shows a yet further embodiment in which a substrate layer 34 is interposed between the end of the optical fiber 2 and the hydrogel 8. It will be seen that the substrate layer 34 has a cavity 36 etched into its underside in order to locate it on the end of the optical fiber 2. This serves to ensure proper lateral location of the hydrogel 8 with respect to the optical fiber 2. It also allows the probe assembly, comprising the substrate layer 34 and hydrogel 8, to be fabricated separately and then mounted to the end of the optical fiber 2. This obviates the need to manipulate the whole fiber during manufacture. The probe may even be assembled onto the optical fiber 2 by an end user, with only the probe assembly being supplied.

It will be appreciated that in this embodiment, there are three boundaries at which the incident light will be reflected. The first is between the optical fiber core 4 and the substrate layer 34; the second is between the substrate layer 34 and the hydrogel 8; and the third is at the upper external boundary 8a of the hydrogel 8.

The three boundaries described above yield three separate interference spectra. One is between the light reflected from the first and second boundaries. The second is generated between light from the second and third boundaries. The second interference pattern yields the previously described measurement of the change in optical path through the hydrogel 8 in response to the target analyte. A third interference spectrum is generated between light from the first and third boundaries. This interface pattern could be used with the first and/or second pattern to improve the measurement accuracy by reducing inherent measurement uncertainty.

The first interference pattern, between the light reflected from the first and second boundaries, can be used to compensate for changes in temperature, assuming that the co-efficient of thermal expansion of the substrate layer 34 is known.

Figure 12B:
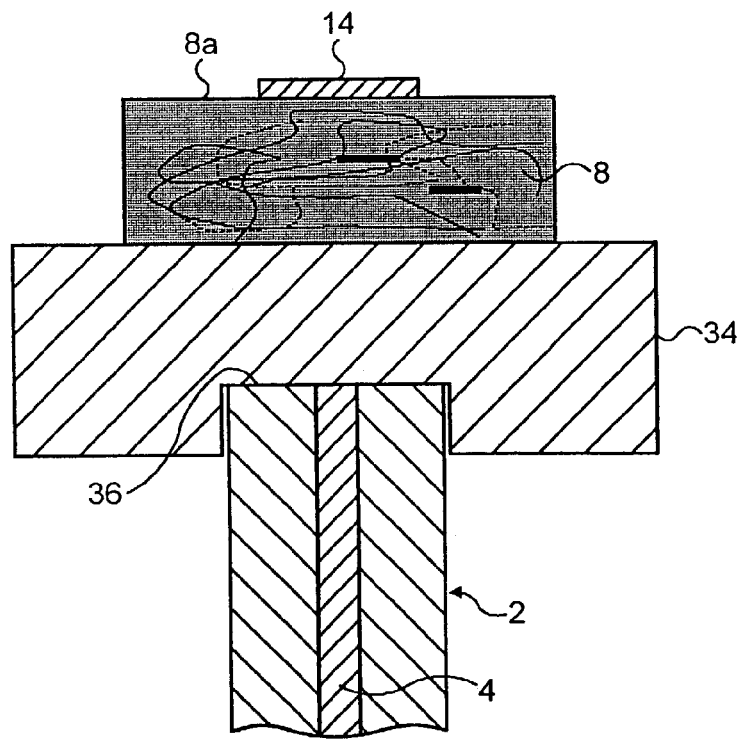

The variant in FIG. 12b is identical to that in FIG. 12a except that a reflector 14 is attached to the upper face of the hydrogel 8.

Figure 13:
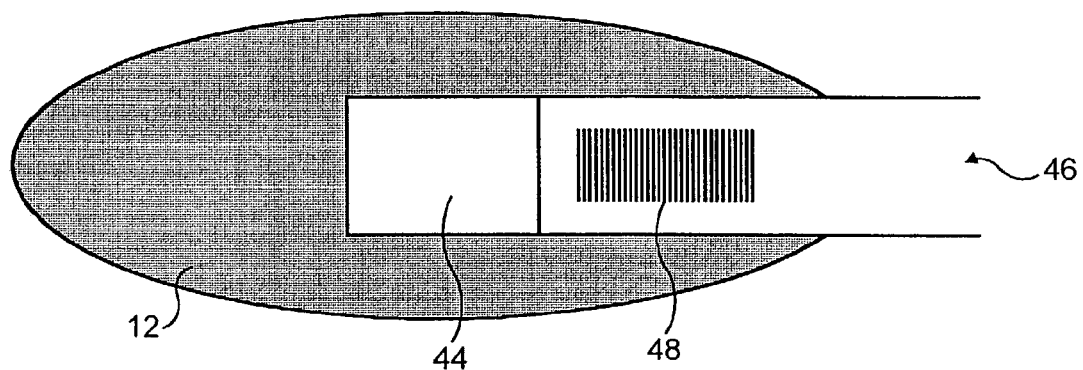
FIG. 13 shows schematically a further embodiment including a reference fiber Bragg grating.

FIG. 13 shows schematically another embodiment of the invention. In this embodiment, the probe comprises a Fabry-Perot sensor 44, of the sort previously described, at the distal end of an optical fiber 46. A fiber Bragg grating 48 is written into the fiber 46 close to the distal end. In use the measured Bragg reflection wavelength indicates the temperature at the end of the fiber 46 which allows this to be taken into account when measuring the response of the Fabry-Perot sensor 44 to the analyte. The fiber Bragg grating gives a wavelength shift of approximately 10 picometres per Kelvin.

Figure 14:
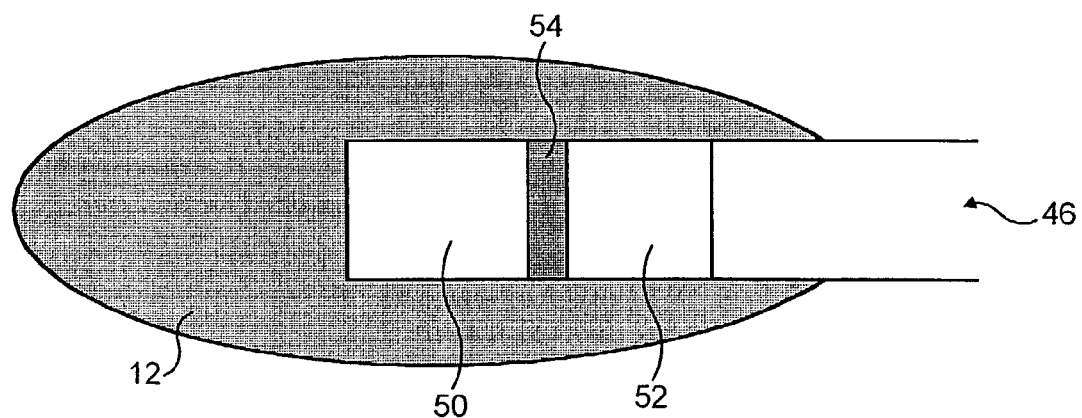
FIG. 14 shows a further schematic embodiment comprising two sensors.

An alternative arrangement embodying compensation for environmental parameters is shown in FIG. 14. In this embodiment first and second Fabry-Perot cavity sensors 50, 52 are provided at the distal end of a fiber 46. The first sensor 50 contains a hydrogel which swells in response to a target analyte. However it also changes volume depending on the temperature, pressure, pH, salt concentrations and presence of other proteins in the analyte solution. The second sensor 52 contains the same hydrogel but without the receptor ligands for the analyte. Thus it does not swell in response to presence of the analyte, but does exhibit the same response to the environmental factors. A partially reflective layer 54 is provided between the two sensors 50, 52 since they are unlikely to differ sufficiently in refractive index to generate a useful reflected beam.

By subtracting the responses of the two sensors, an accurate measurement of the analyte concentration may be obtained.

Figure 15:
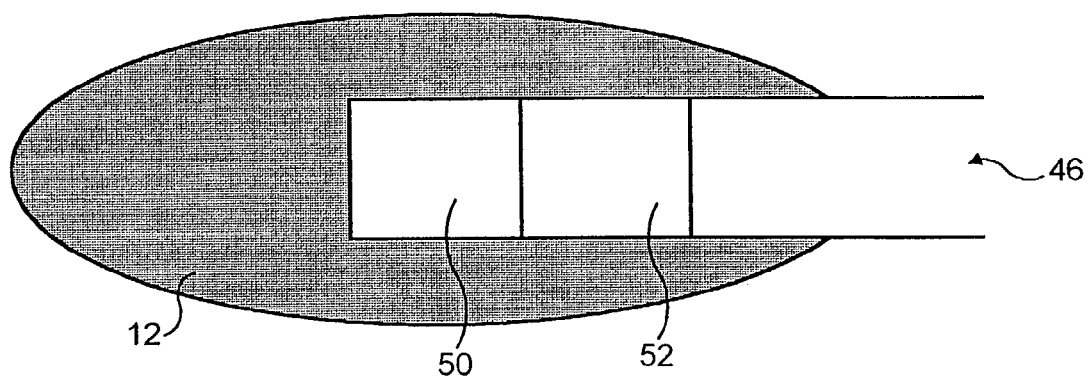
FIG. 15 shows an embodiment similar to FIG. 14 but without a partially reflective layer.

FIG. 15 shows a similar embodiment to FIG. 14 except that the second sensor 52 does not comprise hydrogel but is rather a different polymer. Since the polymer has a known coefficient of thermal expansion, the measurement from the second sensor 52 may be used to account for temperature variations. Since the refractive indices of the two materials used in the two sensors 50, 52 is significantly different, a partially reflecting layer is not essential, although may be desirable to ensure a good quality optical reflection.

Figure 16:
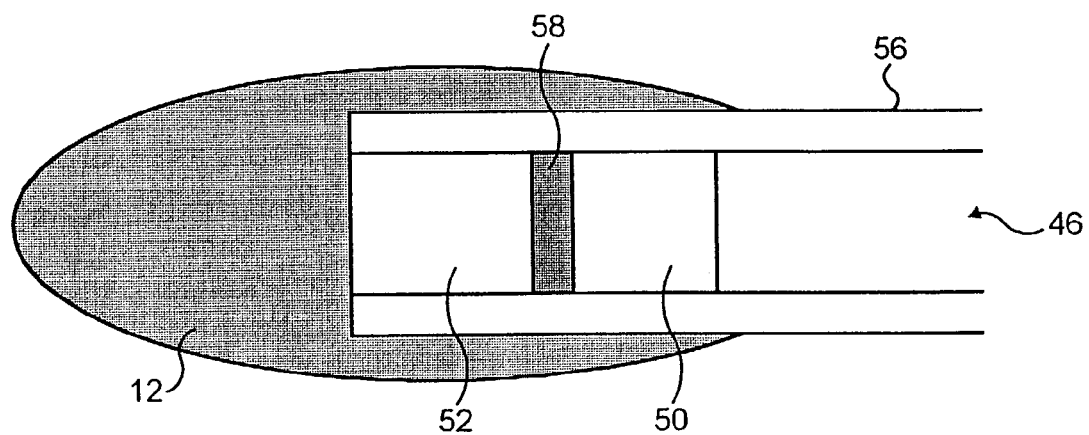
FIG. 16 shows an embodiment similar to FIG. 14 but with a capillary tube.

A further embodiment is shown in FIG. 16. In this embodiment the fiber 46 is encased in a capillary tube 56. The first and second sensors 50, 52 both comprise exactly the same hydrogel and are separated by a partially reflecting layer 58. However in this embodiment the partially reflecting layer 58 also acts as a membrane allowing the analyte solution to pass through but not the analyte molecules. This allows the second sensor to compensate for all environmental parameters e.g. temperature, pH, salinity of the solution.

Figure 17:
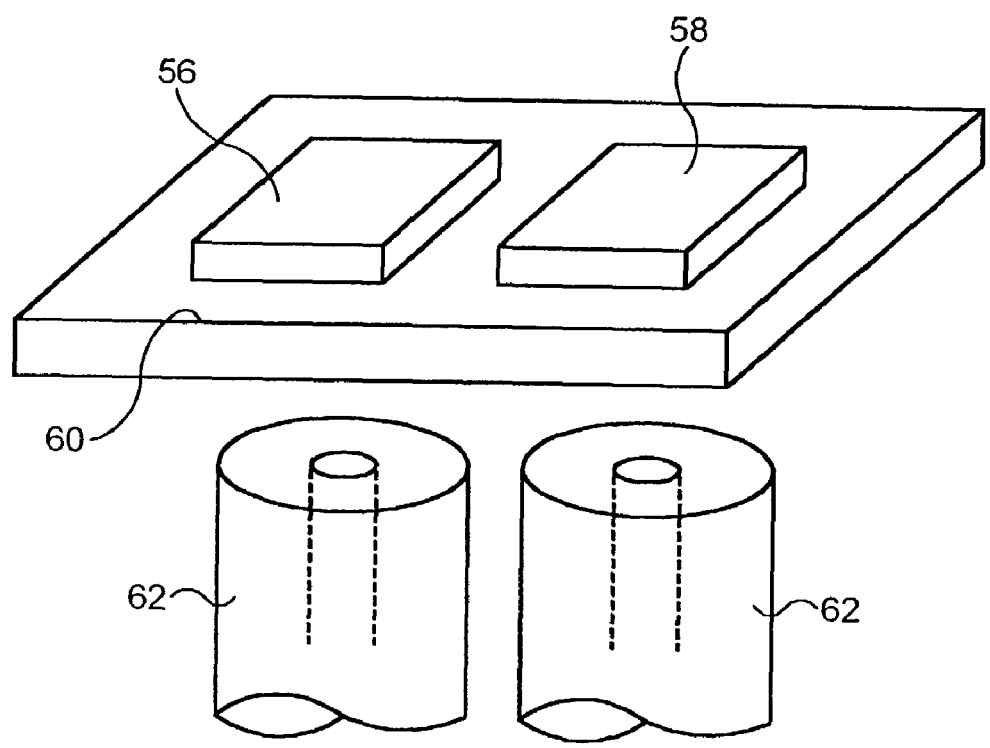
FIG. 17 shows schematically two cavities on a common support.

FIG. 17 shows schematically a probe comprising a measuring Fabry-Perot cavity 56 and a reference cavity 58 provided on a common substrate 60. These are interrogated by a pair of optical fibers 62. Since the optical coupling is from below, the support 60 and measuring material(s) must both be transparent. Alternatively coupling from above could be used or a transmission mode may be employed.

This embodiment provides good compensation since the two cavities 56, 58 are fabricated together and are sufficiently near one another to experience virtually identical environmental conditions.

Of course it should be appreciated that in general, any pair of the probes described hereinabove could be used in a compensation scheme such as that shown in FIG. 17.

Figure 19A:
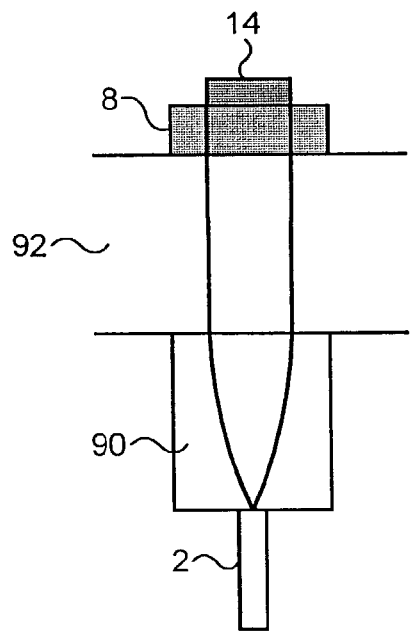
FIGS. 19a and 19b show schematically further embodiments of the invention utilising lenses.
Figure 19B:
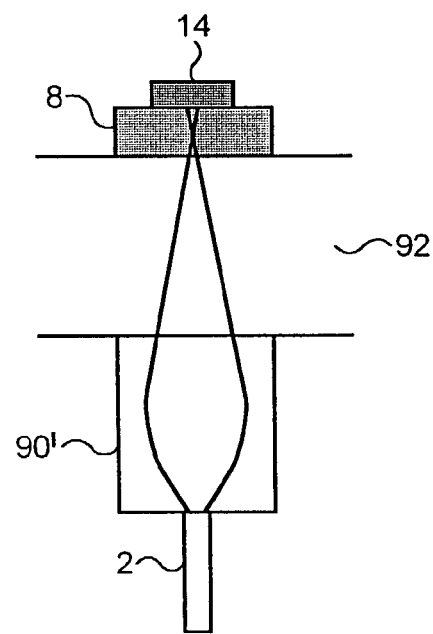

FIG. 19a is a schematic representation of a further embodiment of the invention. This embodiment is similar to that shown in FIG. 12b except that a lens 90 is provided between the optical fiber 2 and the substrate 92. The lens is a graded index (GRIN) type thus causing the light passing through it to follow a curved path. The lens 92 collimates the beam emerging from the fiber 2 into the Fabry-Perot cavity formed by the hydrogel 8. FIG. 19b is identical to FIG. 19a except that a different lens 90' is used which focuses the beam inside the hydrogel layer 8.

The use of a lens 90, 90' allows a thicker substrate to be used since it is no longer constrained by the numerical aperture of the optical fiber.

Figure 20A:
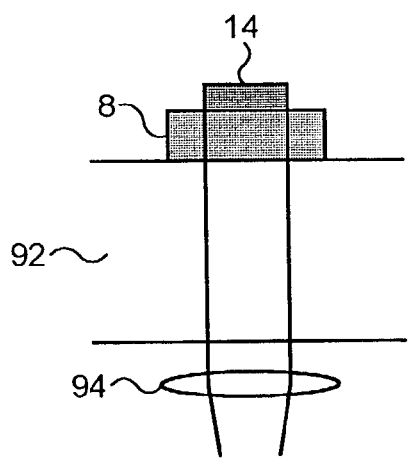
FIGS. 20a and 20b show schematically yet further embodiments which do not use an optical fiber.
Figure 20B:
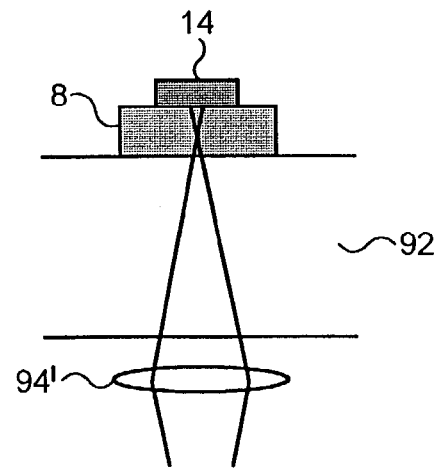

FIGS. 20a and 20b are schematic representations of yet further embodiments of the invention. These are similar to the embodiments of FIGS. 19a and 19b but do not have an optical fiber and utilise an ordinary lens 94, 94 rather than a GRIN lens. As previously, the lens 94 in FIG. 20a collimates the beam into the hydrogel layer 8 whereas the lens 94' of FIG. 20b brings the beam to a focus.

The embodiments of FIGS. 20a and 20b are particularly suited to use in a configuration where the substrate 92, hydrogel 8 and reflector 14 together form a disposable test strip, whereas the lens 94, 94' and associated read-out instrumentation (not shown) is provided in permanent measurement apparatus.

It will be appreciated by those skilled in the art that there are many possible variations on this embodiments herein described. Furthermore, the principles of the invention may have many widely varying applications and are not limited to the examples described. For example, the invention may be used in immunoassays, molecular assays, or in the detection of short DNA and RNA sequences. One particularly preferred application is in the sensing of specific markers produced from muscle hurt during an infarction.

The target analyte may not necessarily be in solution and may be any suitable form of chemical or biological molecule depending upon the cross-linked polymer used.

It will also be appreciated that certain aspects of the invention do not require a cross-linked polymer and thus another suitable measuring material could be provided.

The invention claimed is:

1. An interferometric chemical sensing probe comprising an optical fiber and a chemically responsive measuring material exhibiting a change in volume and/or refractive index in the presence of a given chemical so as to produce an interferometrically measurable change in optical length of at least one interferometric optical path through the probe, wherein said chemically responsive measuring material comprises a hydrogel having a polymer chain and a biomolecular recognition component linked to said polymer chain.

2. An interferometric sensing probe comprising an optical fiber and a measuring material comprising a swollen cross-linked polymer network exhibiting a change in volume and/or refractive index in response to a given measurand so as to produce an interferometrically measurable change in optical length of at least one interferometric optical path through the probe, wherein said polymer network comprises a polymer chain and a biomolecular recognition component linked to said polymer chain.

3. A probe as claimed in claim 1 comprising a Fabry-Perot interferometer having two reflectors, said two reflectors being arranged in said optical path.

4. A probe as claimed in claim 2 comprising a Fabry-Perot interferometer having two reflectors, said two reflectors being arranged in said optical path.

5. A probe as claimed in claim 1 wherein said optical path has a fixed physical length.

6. A probe as claimed in claim 5 wherein a portion of measuring material is provided in a cavity having a fixed-length in a direction parallel to the propagation of measuring light, but wherein said measuring material is free to expand in a direction orthogonal to the propagation of the measuring light.

7. A probe as claimed in claim 5 comprising a wave guide having a core, said core including said measuring material.

8. An optical sensing probe comprising:
a measuring material said measuring material undergoing a change in volume in response to a given measurand; and
a reflector coupled to the measuring material so as to be moved by the measuring material as the measuring material changes in volume, thereby changing the length of a light path through the apparatus, wherein said measuring material comprises a swollen cross-linked polymer network having a polymer chain and a biomolecular recognition component linked to said polymer chain.

9. A probe as claimed in claim 8 wherein:
said reflector has a first side and a second side;
said first side has a first region and a second region;
said first region is coupled to said measuring material; and
said probe is arranged such that in use a beam of light for measuring said measurand is incident upon the reflector on said second region of said first side.

10. A probe as claimed in claim 9 wherein the measuring material is arranged in the form of a hollow cylinder having a central space and wherein said light beam is arranged to pass through said central space to said reflector.

11. A probe as claimed in claim 9 wherein:
said reflector has a first side and a second side;
said first side is coupled to said measuring material; and
said probe is arranged such that in use a beam of light for measuring said measurand is incident upon the second side of said reflector.

12. A probe as claimed in claim 1 arranged such that said optical path through the probe does not include the measuring material.

13. A probe as claimed in claim 1 wherein said optical path includes a measuring cavity comprising a distal reflector formed by a peripheral surface of the measuring material.

14. A probe as claimed in claim 13 comprising:
an optical fiber, said measuring material being provided at an end of the optical fiber;
a first boundary between said optical fiber and said measuring material; and
a second boundary formed by a peripheral surface of the measuring material;
wherein said boundaries form respective reflectors of an interferometer.

15. A probe as claimed in claim 1 comprising compensation means for compensating for environmental parameters.

16. A probe as claimed in claim 2 comprising compensation means for compensating for environmental parameters.

17. A probe as claimed in claim 15 comprising an optical fiber having a fiber Bragg grating written into the optical fiber.

18. A probe as claimed in claim 15 wherein said compensation means comprises a Fabry-Perot interferometer.

19. A probe as claimed in claim 18 wherein said Fabry-Perot interferometer is provided in parallel with an interferometer for measuring a target analyte.

20. A probe as claimed in claim 19 comprising measurement and compensation cavities adjacent one another on a common support.

21. A probe as claimed in claim 20 comprising separate optical fibers for interrogating said cavities.

22. A probe as claimed in claim 15 wherein the swollen cross-linked polymer network is a first cross-linked polymer and wherein the compensation means comprises a second cross-linked polymer with a different response to a target measurand than the first.

23. A probe as claimed in claim 15 comprising an optical fiber having an end and an intermediate substrate layer between the measuring material and the end of the optical fiber.

24. A probe as claimed in claim 23 wherein said substrate layer is provided with means to locate the optical fiber.

25. An interferometric chemical sensing probe comprising an optical fiber and a first chemically responsive measuring material exhibiting a change in volume and/or refractive index in the presence of a given chemical so as to produce a change in at least a first optical path length through the probe; and a second chemically responsive measuring material exhibiting a change in volume and/or refractive index in the presence of a given environmental parameter so as to produce a change in a second optical path length through the probe; wherein said first and second measuring materials are substantially the same, each comprising a hydrogel having a polymer chain and a biomolecular recognition component linked to said polymer chain, and wherein said probe is arranged such that in use said second measuring material does not come into contact with a target analyte.

26. A probe as claimed in claim 25 wherein said first and second measuring materials are provided at a distal end of an optical fiber and separated by a layer which acts to reflect a proportion of light incident on said layer.

27. A probe as claimed in claim 25 comprising a membrane for blocking access of said target analyte to said second measuring material.

28. A probe as claimed in claim 15 wherein said comprising compensation means is provided in series with a measurement part of the probe.

29. A probe as claimed in claim 15 having the measuring material and a compensation material provided coaxially at a distal end of an optical fiber.

30. A probe as claimed in claim 29 wherein said measuring and compensation materials are covered by a membrane sleeve or a capillary tube.

31. A probe as claimed in claim 15 comprising an optical fiber and an intermediate substrate layer between the optical fiber and the measuring material.

32. A probe as claimed in clam 31 comprising an intermediate lens between said substrate and said fiber.

33. Apparatus for sensing a measurand comprising a probe as claimed in claim 1 and read out instrumentation for reading out a measurement of said measurand from said probe.

34. Apparatus for sensing a measurand comprising a probe as claimed in claim 2 and read out instrumentation for reading out a measurement of said measurand from said probe.

35. Apparatus as claimed in claim 34 comprising a scanning filter.

36. An apparatus for sensing a chemical interferometrically comprising a substrate bearing a chemically responsive hydrogel measuring material exhibiting a change in volume and/or refractive index in the presence of a given chemical so as to produce an interferometrically measurable change in at least one optical path length through the apparatus, an optical fiber, and at least one lens between the optical fiber and substrate through which in use light traversing said optical path length passes.

37. An interferometric chemical sensing probe comprising an optical fiber and a chemically responsive measuring material, said material exhibiting a change in volume and/or refractive index in the presence of a given chemical so as to produce an interferometrically measurable change in optical length of at least one interferometric optical path through the probe, wherein said chemically responsive measuring material comprises a swollen cross-linked polymer network, said polymer network comprising polymer chains having cross links, and wherein additional cross-links are formed between antibodies and antigens or peptide sequences immobilised on the polymer chains.

38. Sensing apparatus comprising a probe as claimed in claim 1 wherein said optical path forms at least a part of a laser cavity.

39. Sensing apparatus comprising a probe as claimed in claim 2 wherein said optical path forms at least a part of a laser cavity.

40. A method of sensing a chemical comprising providing a probe including a measuring material that changes in volume and/or refractive index in the presence of said chemical, exposing said measuring material to said chemical and measuring interferometrically the resulting change in an optical path length through the probe, wherein said measuring material comprises a swollen cross-linked polymer network having a polymer chain and a biomolecular recognition component linked to said polymer chain, and reading out a measurement related to said resulting change.

41. A method as claimed in claim 40 comprising measuring a reflection spectrum using a scanning filter.

42. A method of forming a gel on the end of an optical fiber comprising immobilising a pre-gel material on said fiber end, covering said pre-gel material with a lid, performing a gelation of the pre-gel material to form a gel and removing said lid.

43. A method as claimed in claim 42 comprising constraining the pre-gel material laterally.

44. A method as claimed in claim 42 comprising using a capillary tube or a cylinder cast to constrain said pre-gel material laterally.

45. A method as claimed in claim 44 wherein said cylinder cast comprises part of a fiber optic connector.

46. A method as claimed in claim 43 comprising forming a separate probe element comprising the measuring material and subsequently mounting said probe element to an optical fiber.

47. An interferometric sensing probe comprising an optical fiber and a measuring material comprising a cross-linked polymer exhibiting a change in volume and/or refractive index in response to a given measurand so as to produce an interferometrically measurable change in at least one interferometric optical path length through the probe, wherein said measuring material comprises a biomolecular recognition component.

48. A probe as claimed in claim 47, wherein said cross-linked polymer is a hydrogel.

49. An interferometric chemical sensing probe for use with an optical fiber, said probe comprising a chemically responsive measuring material exhibiting a change in volume and/or refractive index in the presence of a given chemical so as to produce an interferometrically measurable change in optical length of at least one interferometric optical path through the probe, wherein said chemically responsive measuring material comprises a swollen cross-linked polymer network having a polymer chain and a biomolecular recognition component linked to said polymer chain.

50. An interferometric sensing probe for use with an optical fiber, said probe including a measuring material that comprises a swollen cross-linked polymer network, said network comprising a biomolecular recognition component exhibiting a change in volume and/or refractive index in response to a given measurand so as to produce an interferometrically measurable change in optical length of at least one interferometric optical path through the probe.

51. An interferometric chemical sensing probe for use with an optical fiber, said probe comprising a first chemically responsive measuring material a exhibiting a change in volume and/or refractive index in the presence of a given chemical so as to produce an interferometrically measurable change in at least a first optical path length through the probe; and a second chemically responsive measuring material exhibiting a change in volume and/or refractive index in the presence of a given environmental parameter so as to produce an interferometrically measurable change in a second optical path length through the probe; wherein said first and second measuring materials are substantially the same, each comprising a hydrogel having a polymer chain and a biomolecular recognition component linked to said polymer chain, and wherein said probe is arranged such that in use said second measuring material does not come into contact with a target analyte.

52. An interferometric sensing probe for use with an optical fiber, said probe comprising a measuring material comprising a crosslinked polymer exhibiting a change in volume and/or refractive index in response to a given measurand so as to produce an interferometrically measurable change in at least one interferometric optical path length through the probe, wherein said measuring material comprises a biomolecular recognition component.

* * * * *

UNITED STATES PATENT AND TRADEMARK OFFICE
CERTIFICATE OF CORRECTION

| | | |
|---|---|---|
| PATENT NO. | : 7,440,110 B2 | Page 1 of 1 |
| APPLICATION NO. | : 10/273483 | |
| DATED | : October 21, 2008 | |
| INVENTOR(S) | : Dag R. Hjelme et al. | |

It is certified that error appears in the above-identified patent and that said Letters Patent is hereby corrected as shown below:

Column 15, line 52, please delete "clam" and insert -- claim --.
Column 16, line 41, please delete "42" and insert -- 43 --.
Column 16, line 46, please delete "43" and insert -- 42 --.
Column 18, line 12, please delete "crosslinked" and insert -- cross-linked --.

Signed and Sealed this

Third Day of February, 2009

JOHN DOLL
*Acting Director of the United States Patent and Trademark Office*